(12) United States Patent
Hunter

(10) Patent No.: US 11,161,174 B2
(45) Date of Patent: Nov. 2, 2021

(54) METHOD AND APPARATUS FOR CONVEYING SAND MOLDS

(71) Applicant: HUNTER FOUNDRY MACHINERY CORPORATION, Schaumburg, IL (US)

(72) Inventor: William Gary Hunter, Barrington, IL (US)

(73) Assignee: HUNTER FOURNDRY MACHINERY CORPORATION, Schaumburg, IL (US)

( * ) Notice: Subject to any disclaimer, the term of this patent is extended or adjusted under 35 U.S.C. 154(b) by 0 days.

(21) Appl. No.: 16/720,307

(22) Filed: Dec. 19, 2019

(65) Prior Publication Data

US 2020/0198002 A1 Jun. 25, 2020

Related U.S. Application Data

(60) Provisional application No. 62/782,818, filed on Dec. 20, 2018.

(51) Int. Cl.
*B22D 33/00* (2006.01)
(52) U.S. Cl.
CPC .................. *B22D 33/00* (2013.01)
(58) Field of Classification Search
CPC ...... B22D 30/00; B22D 30/005; B22D 47/00; B22D 47/02
See application file for complete search history.

(56) References Cited

U.S. PATENT DOCUMENTS

| | | |
|---|---|---|
| 4,224,979 A | 9/1980 | Rosin et al. |
| 4,589,467 A | 5/1986 | Hunter |
| 4,934,511 A | 6/1990 | Wood, III et al. |
| 5,022,512 A | 6/1991 | Hunter |
| 7,637,303 B2 | 12/2009 | Hunter |
| 2002/0069999 A1 | 6/2002 | Hackman et al. |
| 2004/0026061 A1 | 2/2004 | Hamilton et al. |
| 2008/0029238 A1 | 2/2008 | Hunter |
| 2013/0146422 A1 | 6/2013 | Hunter |
| 2017/0297091 A1 | 10/2017 | Hunter et al. |

FOREIGN PATENT DOCUMENTS

GB 1330438 9/1973

OTHER PUBLICATIONS

293 "Know-How on Automation": Transfer—1: https://www.misumi-techcentral.com/tt/en/lca/2017/06/293-know-how-on-automation-transfer-1.html, Jul. 21, 2017 (2 pages).

(Continued)

*Primary Examiner* — Kevin P Kerns
*Assistant Examiner* — Steven S Ha
(74) *Attorney, Agent, or Firm* — Pauley Erickson & Swanson

(57) ABSTRACT

Method and apparatus for feeding sand molds laterally and/o between stations of differing heights. The method and apparatus of this invention utilize walking-beam-type conveyors having spaced apart fixed outboard rails and a central reciprocating rail. Walking-beam conveyors can be disposed in perpendicular directions with a junction therebetween that allows for a perpendicular change in direction. The method and apparatus of this invention include lift, leveling, and/or lateral transfer mechanisms for lateral placement of the stations relative to the conveyance path.

20 Claims, 10 Drawing Sheets

(56) References Cited

OTHER PUBLICATIONS

U.S. Patent Office, English language version of the International Search Report, Form PCT/ISA/210 for International Application PCT/US2019/067760, dated Mar. 25, 2020 (4 pages).
U.S. Patent Office, English language version of the Written Opinion of the ISA, Form PCT/ISA/237 for International Application PCT/US2019/067760, dated Mar. 25, 2020 (10 pages).

METHOD AND APPARATUS FOR CONVEYING SAND MOLDS

CROSS REFERENCE TO RELATED APPLICATION

This application claims the benefit of U.S. Provisional Application, Ser. No. 62/782,818, filed on 20 Dec. 2018. The parent application is hereby incorporated by reference herein in its entirety and is made a part hereof, including but not limited to those portions which specifically appear hereinafter.

BACKGROUND OF THE INVENTION

Field of the Invention

This invention is directed to conveyors for feeding sand molds for metal casting from one machine, such as a forming machine, to a second machine, such as a metal pouring station. The invention provides a method and apparatus for automatically and continually feeding prepared sand molds using walking beam-type mold conveyors.

Discussion of Related Art

Molded metal castings are commonly manufactured at foundries through a matchplate molding technique which employs green sand molds comprised of prepared sand and additives which are compressed around cope and drag patterns mounted on opposite sides of a matchplate. The sand mold is thus formed in upper and lower matching portions, an upper cope mold, and a lower drag mold. The cope mold is formed in a separate cope flask which is filled with prepared sand and compacted onto the matchplate. The matchplate is then removed leaving an indentation in the cope mold of the desired shape for the upper portion of the casting. Simultaneously, the drag mold is formed in a separate drag flask. Usually the matchplate is in the form of a planar member with the pattern for the cope mold on one side and the pattern for the drag mold on the other. After the cope and drag molds have been formed, they are placed together to form a unitary mold having an interior cavity of the desired shape. The cavity can then be filled with molten metal through an inlet or "sprue" provided in the cope mold to create the desired casting. Such a system is disclosed in U.S. Pat. No. 5,022,2 issued to Hunter, herein incorporated by reference.

As with many volume sensitive production operations, manufacturers are required to automate the manufacturing process in order to remain competitive. Foundries engaging in the casting of metal objects through the use of green sand molds are not immune to this reality. It is common in today's marketplace, for the machine which produces the sand molds to be connected to a machine which fills the sand mold with molten metal, which in turn is connected to a machine for cooling the molten metal into a solid casting, which in turn is connected to a machine for removing the sand mold and revealing the casting for harvest. Such a system is disclosed in U.S. Pat. No. 4,589,467, issued to Hunter, herein incorporated by reference.

In the aforementioned '467 Patent, the sand molds are manufactured and communicated along a linear conveyor to a circular, rotating, or "carousel" conveyor. Molten metal is introduced into the molds at one location on the carousel and the molten metal is then allowed to cool within the sand mold as the carousel rotates. The carousel is provided with both an outer diameter track and an inner diameter track which provides for additional cooling of the metal, and which increase the throughput of the machine.

U.S. Pat. No. 7,637,303, issued to Hunter, herein incorporated by reference, discloses a walking beam-type mold conveyor. There is a continuing need for an improved conveyor system for transporting sand molds from the machine that produces the sand mold to, for example, the carousel conveyor, particularly for machines not originally designed to be used together.

SUMMARY OF THE INVENTION

A general object of the invention is to provide a mold conveyor that feeds molds from an origin, e.g., a mold forming device, to a destination, e.g., a metal pouring station. The general object of the invention can be attained, at least in part, through a method for conveying a sand mold with an accumulating conveyor. The accumulating conveyor includes one or more walking-beam-type conveyors that includes a transfer rail movable with respect to at least one stationary fixed rail.

In embodiments of this invention, the method and apparatus for conveying sand molds begins by depositing a first sand mold on a transfer conveyor, such as from a sand mold forming device in combination with the first transfer conveyor. The transfer conveyor includes two outboard rails and a central transfer rail movable between the two outboard rails. The first sand mold moves along the first transfer conveyor in a first direction and is placed on a first junction resting station. The first junction resting section is at a downstream end of the first transfer conveyor, and can be a transfer station to a second machine or an upstream end of a second transfer conveyor, which similarly includes two outboard rails and a central transfer rail movable between the two outboard rails.

The invention further provides a method and apparatus for moving a sand mold onto and/or off of an accumulating conveyor in a direction lateral to a conveying direction of the accumulating conveyor. In embodiments of this invention, the depositing of the sand mold on the transfer conveyor is done from the side, or perpendicular to the transfer conveyor conveyance path. In other words, the sand mold is pushed, slid, or otherwise moved onto the transfer conveyor first over one of the stationary side rails in a direction toward the middle rail and other side rail.

Embodiments of this invention include an adjustable transfer rail that allows for vertical adjustment between the two outboard rails. Any vertical height differences between the center and outboard rails can impact mold integrity during side entry due to impact of any slightly offset height between the rails. The adjustable transfer rail can include a leveler, such as including a height adjustment cylinder for leveling or otherwise adjusting the transfer rail into plane or other suitable height with respect to the outboard rails.

Embodiments of this invention include a pusher mechanism is used to transfer the sand mold from the conveyor end (e.g., second junction resting station) to, for example, a metal pouring station. The pusher mechanism of embodiments of this invention includes a lateral push-path that is perpendicular to the conveyor path, thereby allowing the mold to exit the conveyor to the side instead of at the end colinear with the conveyance path. The pusher mechanism can include a pusher bar or blade that travels from the side first across one of the outboard rails and then across the transfer rail to move the mold laterally off the conveyor.

The invention further includes an apparatus for conveying a sand mold that includes a transfer station at a downstream end of an accumulating conveyor. The transfer station includes a mold lift platform and a pusher, wherein the mold lift platform is configured to raise the sand mold off the at least one fixed rail into a position adjacent the pusher. The mold lift platform can be adapted to lower below the fixed rail(s) to allow the transfer rail to move the sand mold into position over the mold lift platform. The transfer station can include a frame extending above the accumulating conveyor, whereby the mold lift platform moves vertically along the frame, and the pusher is pivotably connected to an upper section of the frame.

The invention further includes a method for conveying a sand mold. The method includes: moving the sand mold with an accumulating conveyor via a transfer rail reciprocating with respect to at least one fixed rail; and moving the sand mold onto and/or off of the accumulating conveyor in a direction lateral to a conveying direction of the accumulating conveyor and/or at different vertical heights. Embodiments of the invention include step of pushing the sand mold with a pusher that travels in the direction lateral to the conveying direction. Embodiments of the invention include a step of adjusting a horizontal alignment of the transfer rail with respect to at least one fixed rail, such as by moving a leveling cylinder under the transfer rail vertically in a direction perpendicular to the conveying direction.

Embodiments of the invention include steps of moving the sand mold to a transfer station at an end of the accumulating conveyor, and lifting the sand mold to a pusher. The transfer station desirably includes a mold lift with a cross-shape or X-shape lift platform, formed by two perpendicular extensions that extend between pairs of four corner pads of an accumulating conveyor end. During use, the method includes lowering a mold lift platform below the at least one fixed rail, and moving the transfer rail with the sand mold into position over the lift platform. These and other objects and features of this invention will be better understood from the following detailed description taken in conjunction with the drawings.

DEFINITIONS

Within the context of this specification, each term or phrase below will include the following meaning or meanings.

References herein to "conveying combination" are to be understood to refer to a combination of two elements, such as two conveyors, whereby an item conveyed by one element is transferable to the other element for continued conveyance to the intended destination.

References herein to "upstream" and "downstream" are to be understood with reference to directions of travel of molds on a conveyor. "Upstream" refers to a direction toward a place of origin, such as a mold forming device, and "downstream" refers to a direction toward a place of destination.

DESCRIPTION OF PREFERRED EMBODIMENTS

Figure 1:
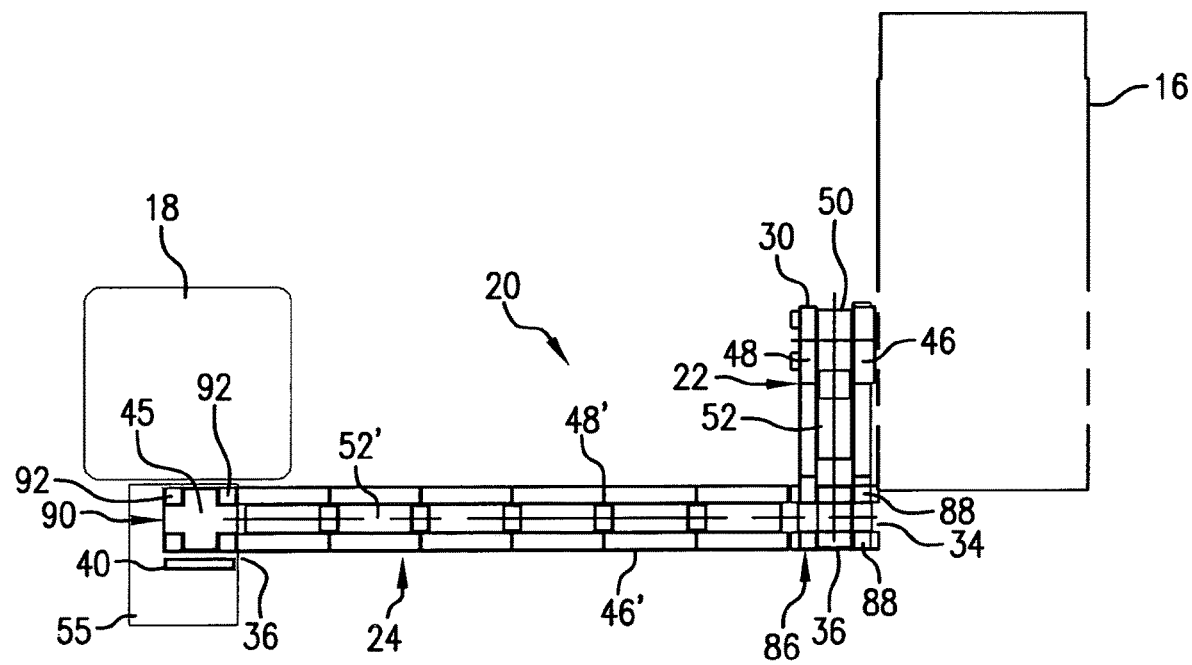
FIG. 1 is a top view of an accumulating mold conveyor according to one embodiment of this invention.

Referring to FIG. 1, this invention provides a conveyor assembly, shown as accumulating mold conveyor 20, for transporting sand molds from a first station 16, such as a sand mold forming station, to a second station 18, such as a metal pouring station.

Accumulating mold conveyor 20 includes first transport conveyor 22 oriented in a first direction, and second transfer conveyor 24 oriented in a second direction. As will be appreciated, the invention can be applied to an accumulating conveyor with only one transfer conveyor or more than two. In the embodiment of FIG. 1, first and second transfer conveyors 22 and 24 are disposed perpendicular to each other; however, the conveyors of this invention can be disposed at other angles, depending on need. First transfer conveyor 22 has an upstream end 30 that is to be disposed toward first station 16, and a downstream end 32 opposite the upstream end 30. Similarly, second transfer conveyor 24 has an upstream end 34 and an opposing downstream end 36. Sand molds travel along the conveyors of this invention from an upstream end to a downstream end. Downstream end 32 of first transfer conveyor 22 is in conveying communication with upstream end 34 of second transfer conveyor 24, such that a sand mold is transferred during operation from downstream end 32 of first transfer conveyor 22 to upstream end 34 or second transfer conveyor 24.

First transfer conveyor 22 includes first outboard rail 46 spaced apart from second outboard rail 48. Outboard rails 46 and 48 can each be formed as a single rail member or from a plurality of smaller individual rail members. A central rail channel 50 is formed between first outboard rail 46 and second outboard rail 48. Central transfer rail 52 is disposed within central rail channel 50, and is movable therein and between the two fixed outboard rails 46 and 48. Second transfer conveyor 24 includes components identical or at least similar to first transfer conveyor 22. These components are described with reference to first transfer conveyor 22, and identified by element reference numbers associated with a prime (').

A pusher station 55 is disposed at the end 36 of the second transfer conveyor 24. The pusher station 55 includes a pusher 40 that moves each mold from the conveyor 24 to the second station 18. As shown in FIG. 1, each of the stations 16 and 18 are located laterally relative to the conveyor ends 30 and 36 respectively. The pusher moves in a direction perpendicular to the conveyance direction of the second transfer conveyor 22 to push the mold onto the second station 18. An optional lift mechanism with a lift plate or platform 45 can be used if the second station 18 is at a different height from the first station 16, such as shown in FIG. 2.

The accumulating mold conveyor of this invention is not limited to the configuration and number of fixed and moveable rails shown in FIG. 1. For example, the center rail(s) can be fixed in place and not moveable, with two or more outboard rails moveable with respect to the fixed center rail(s). Also, in one embodiment of the invention, two moveable transfer rails are disposed on either side of a fixed center rail, and each of the moveable transfer rails is between the center rail and a further fixed outboard rail (e.g., five total rails).

Figure 2:
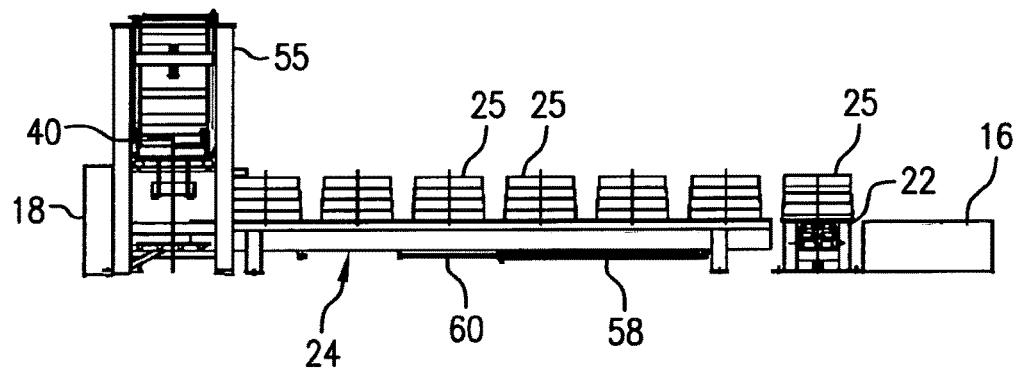
FIG. 2 is a side view of an accumulating mold according to one embodiment of this invention.

FIG. 2 is a side view of accumulating mold conveyor 20 showing molds 25 thereon. As shown in FIG. 2, the second station 18 has a receiving surface that is higher than the mold conveyor 20. The height of the mold conveyor 20 is chosen due to the height of first station 16, and in FIG. 2, the pusher station 55 is incorporated into or with a lift mechanism, such as discussed further below, forming a lift and transfer station 55. As will be appreciated, the lift station could additionally or alternatively be incorporated elsewhere along the conveyor, such as at the end near the first station or at a junction of two or more conveyors, depending on need.

Figure 3:
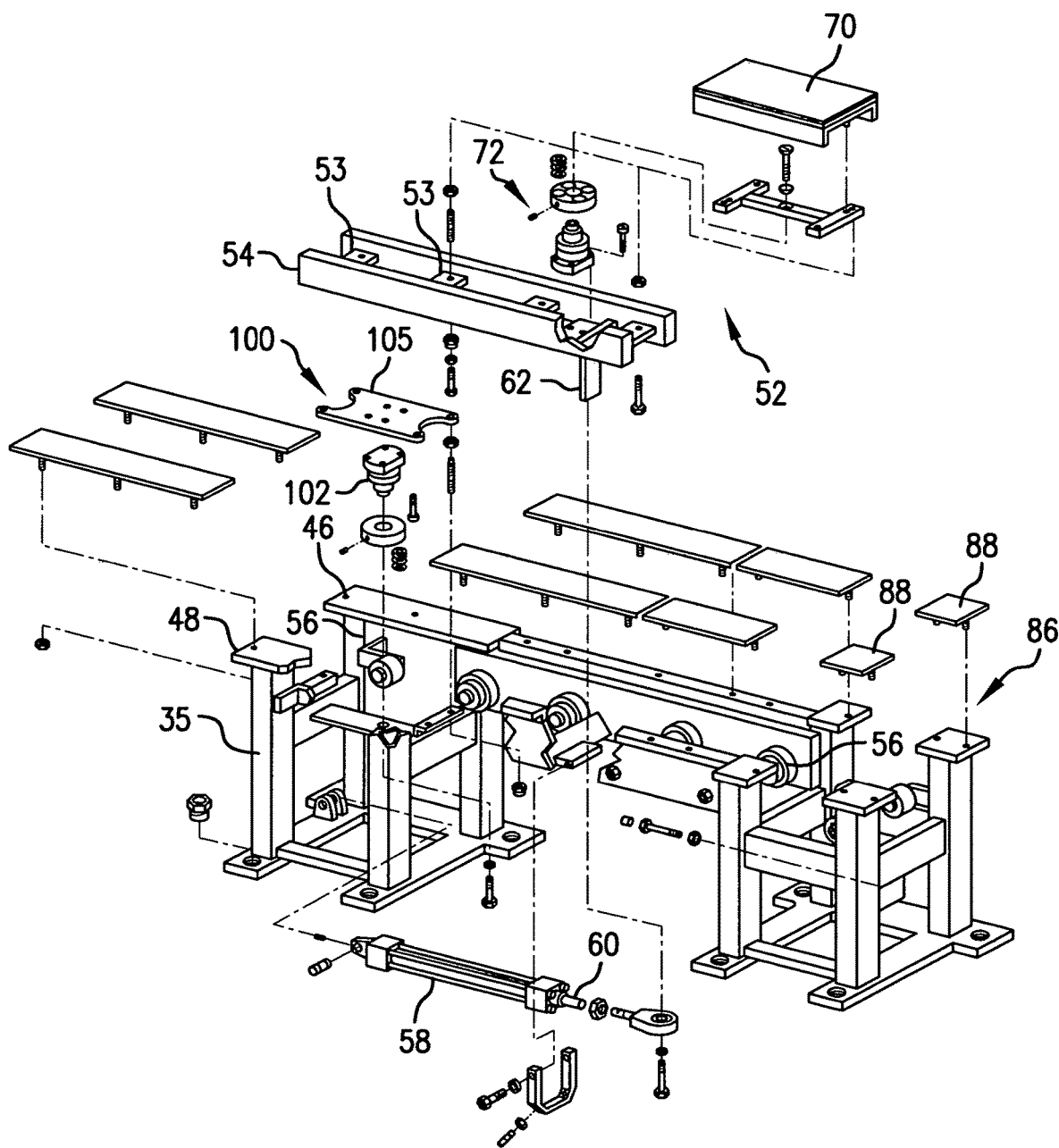
FIGS. 3 and 4 each illustrate an accumulating mold conveyor section according to one embodiment of this invention.
Figure 4:
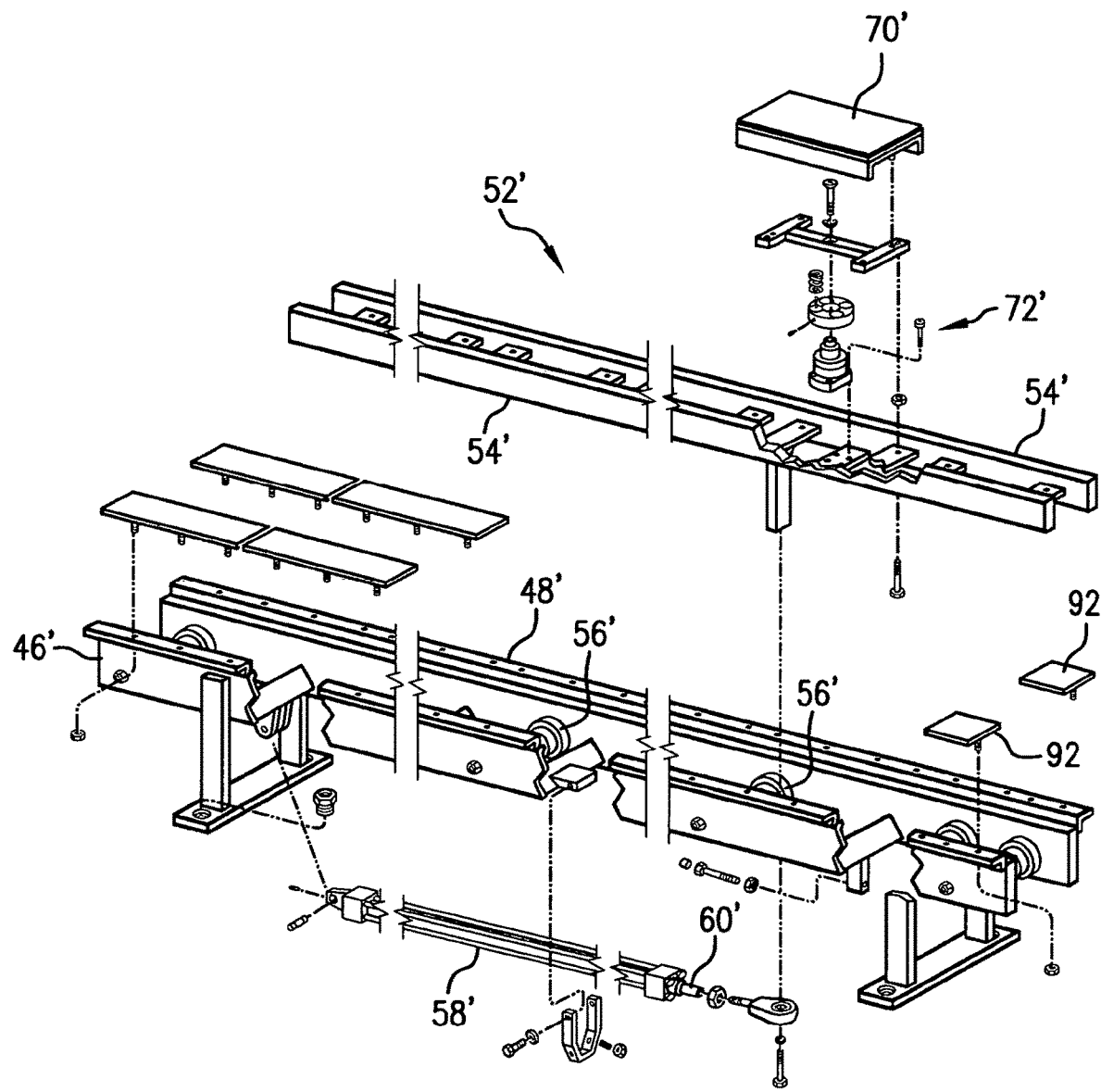

As shown in FIG. 3, the central transfer rail 52 is a reciprocating rail that includes a rail frame 54, including crossbars 53, disposed upon a plurality of rollers 56. Each transfer conveyor includes at least one pressurized fluid piston 58, e.g., a hydraulic piston, having a moveable piston arm 60 connected to frame 54 by connector 62. Piston arm 60, and thus frame 54 and central transfer rail 52, is movable between an upstream position and a downstream position. In embodiments of this invention, the central transfer rail is movable between three positions, a central position, an upstream position, and a downstream position.

A plurality of sand mold carrier plates 70 is disposed along the frame 54. Each of carrier plates 70 is attached to the rail frame 54 by one of a plurality of pressurized fluid lift mechanisms 72, e.g., a pneumatically actuated piston. Each of pressurized fluid lift mechanisms 72 is adapted to lift a corresponding one of carrier plates 70, and a sand mold thereon, to a lifted position above or higher than the outboard rails 46 and 48, and then to lower the corresponding one of carrier plates 70 to lowered position. In the lowered position, sand molds 25 are disposed on outboard rails 46 and 48. In the lifted position, sand molds 25 are moved to, and then lowered onto, a downstream position on outboard rails 46 and 48.

The lifting distance of the sand molds 25 can vary depending on need. In one embodiment of this invention, the sand molds 25 are lifted less than an inch above the outboard rails 46 and 48, and more desirably about $1/16^{th}$ of an inch. In another embodiment, the sand molds are not actually lifted off the outboard rails, but the carrier plates place upward pressure on the sand molds to reduce friction and allow the sand molds to more easily slide along the outboard rails.

Sand molds 25 are moved along first transfer conveyor 22 by lifting a sand mold 25 off outboard rails 46 and 48 at a first of resting positions with a corresponding one of carrier plates 70, moving the sand mold in a downstream direction with central transfer rail 52 to dispose sand mold 25 over a second of resting positions 80, and lowering sand mold 25 onto outboard rails 46 and 48 at the second of resting positions 80. Central transfer rail 52 then moves back to the first position, and the process repeats to incrementally move, or "walk," sand mold 25 in a downstream direction on first transfer conveyor 22.

Referring to FIGS. 1 and 2, lateral entry of the molds 25 onto the conveyor 20 provides additional issues over colinear end entry. Moving the molds from the side can result in a lower leading edge of the mold catching on the rails, particularly the outboard rail on the Par side from the entry point. This is due to a lower position of the central rail between the outboard rails. Embodiments of this invention include an adjustment mechanism for the central rail, to lift the central rail even with the outboard rails, at least at the entry position.

Figure 5:
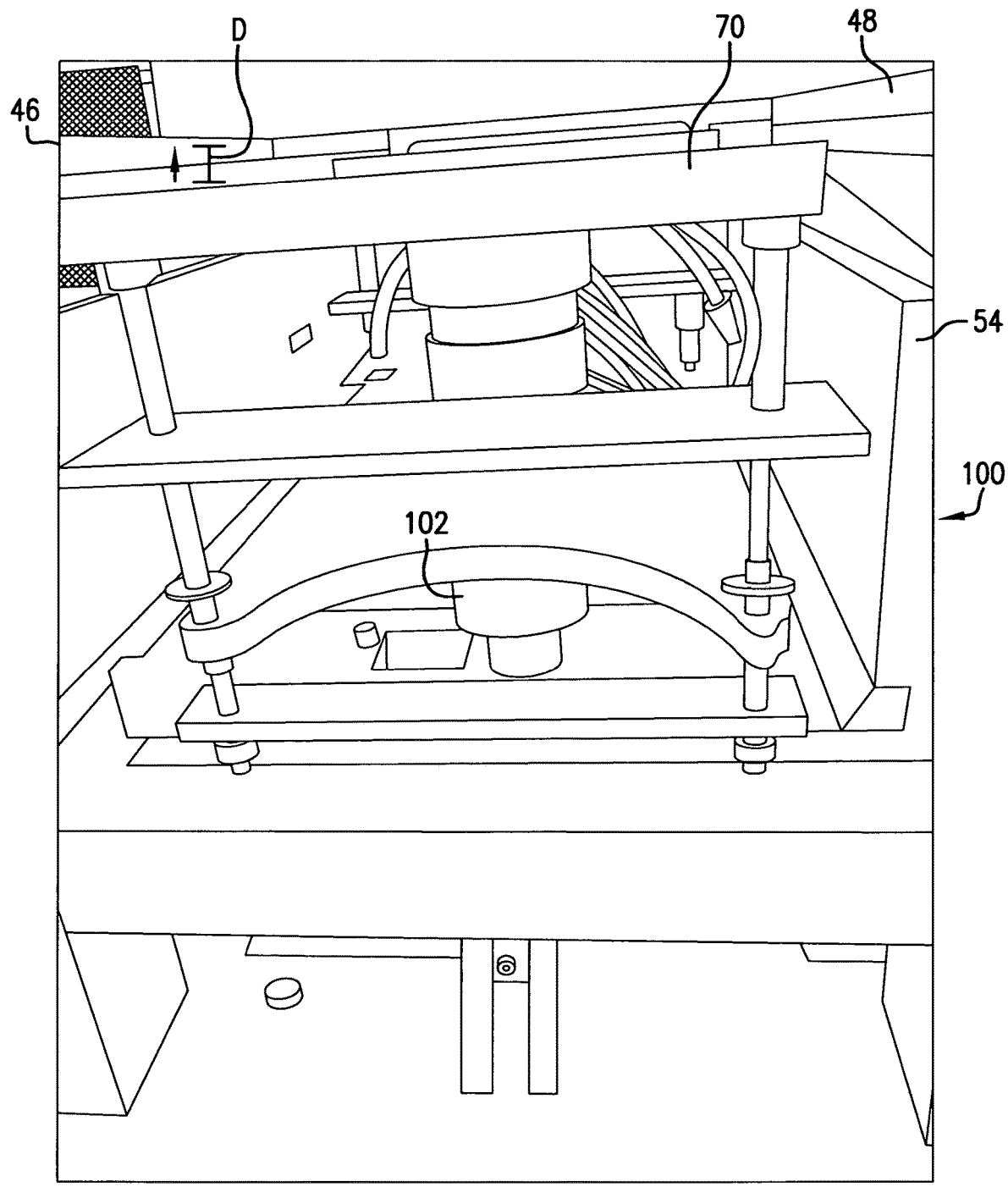
FIG. 5 shows a leveling or adjusting mechanism according to one embodiment of this invention.
Figure 6:
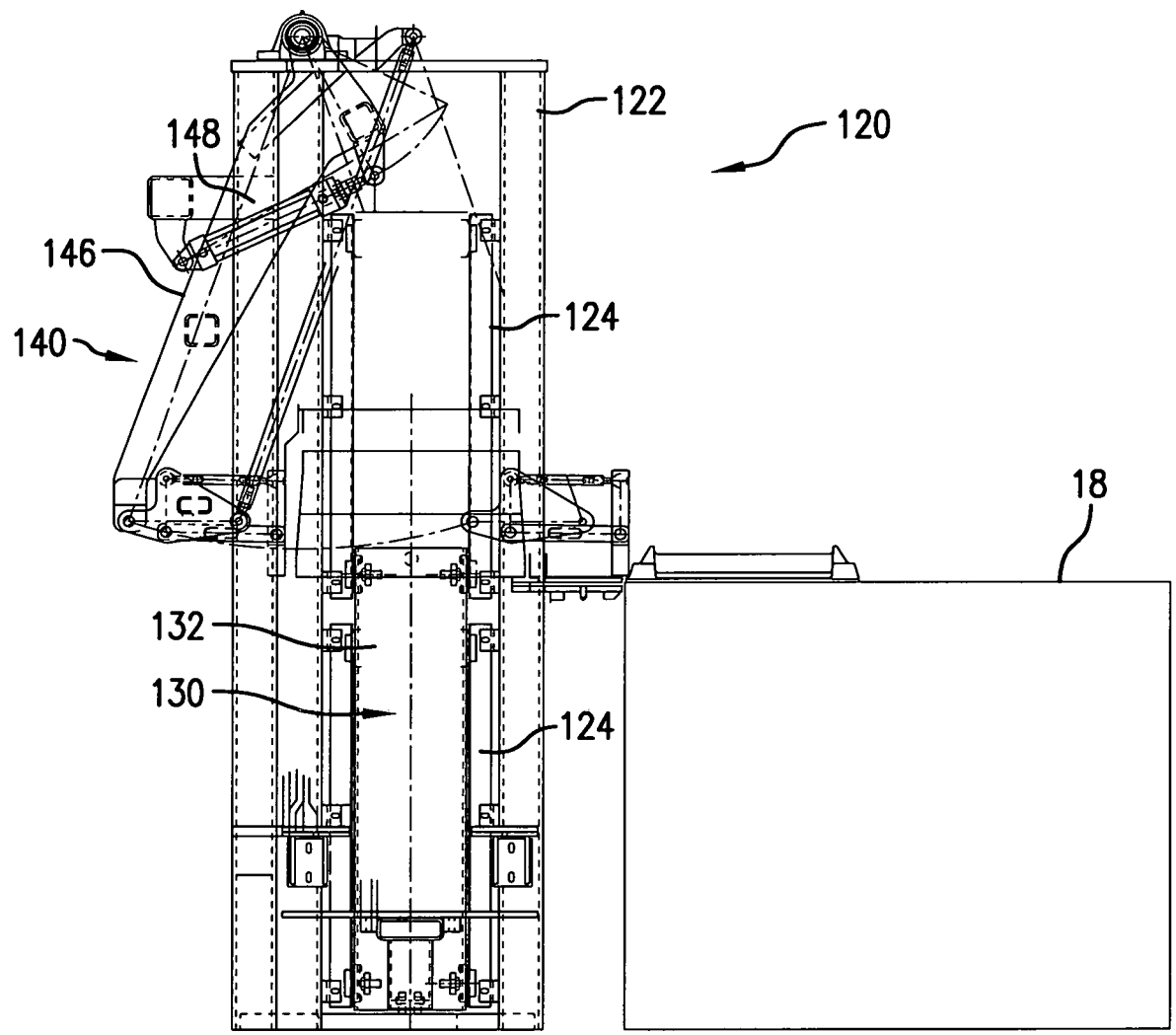
FIGS. 6-11 illustrate a lift and transfer mechanism according to one embodiment of this invention.

FIGS. 3 and 5 show an adjustment mechanism 100 in combination with the first transfer rail 52. The mechanism includes a leveling cylinder 102 on the conveyor frame 35 that provides vertical movement (or perpendicular to the conveying direction) of the end of the first transfer rail 52. The cylinder 102, connected by plate 105 to crossbars 53, raises the rail frame 54 to level a first pad 70 with the corresponding outboard rail 48, such as shown by distance D in FIG. 5. The frame 54 may be lifted off rollers 56, and then lowered again after the mold 25 is in the conveying position on the conveyor 20.

A plurality of optional sensor mechanisms can disposed along each transfer conveyor. Each of the plurality of sensor mechanisms is desirably disposed in sensing combination with one of resting positions. Sensor mechanisms detect the presence of sand molds along the transfer conveyor, and can be used to actuate lifting of a corresponding carrier plate when a sand mold is disposed above the corresponding carrier plate. Thus, in one embodiment of this invention, a carrier plate is not lifted unless a sand mold is present above. Various and alternative sensor mechanisms are available for the use in the accumulating mold conveyor of this invention, such as, without limitation, motion sensors using visible or infrared light or weight sensors disposed beneath outboard rails.

Referring to FIG. 1, accumulating mold conveyor 20 includes first junction resting station 86 disposed between downstream end 32 of first transfer conveyor 22 and upstream end 34 of second transfer conveyor 24. Junction resting station 86 includes four resting pads 88 adapted to hold a sand mold thereon. Each of resting pads 88 is spaced apart from another of the resting pads, and disposed at one of the corners of junction resting station 86. The spacing between each of resting pads 88 is such that central transfer rail 52 is movable between the spaced apart resting pads 88, as shown in FIG. 1, and able to lower sand mold 25 onto resting pads 88. When the central transfer rail 52 of first transfer conveyor 22 is moved out from first junction resting station 86, central transfer rail 52' of second transfer conveyor 24 is moved between the spaced apart resting pads 88. When positioned within first junction resting station 86, central transfer rail 52' of second transfer conveyor is able to lift sand mold 25 off resting pads 88, thereby perpendicularly transferring sand mold 25 to second transfer conveyor 24.

As will be appreciated by those skilled in the art following the teachings herein provided, the number and configuration, e.g., placement, of the resting pads of the junction resting stations will depend on the configuration of the transfer conveyors, e.g., the number of rails and which rail(s) is/are moveable, as discussed above. Also, the invention is not limited to the particular accumulating mold conveyors shown in FIG. 1. Additional types of accumulating mold conveyors, such as are known in the art, can be used with the junction resting stations according to this invention to impart directional change, such as, for example, the conveyors of U.S. Pat. No. 4,890,664, issued to Hunter, and herein incorporated by reference.

Figure 11:
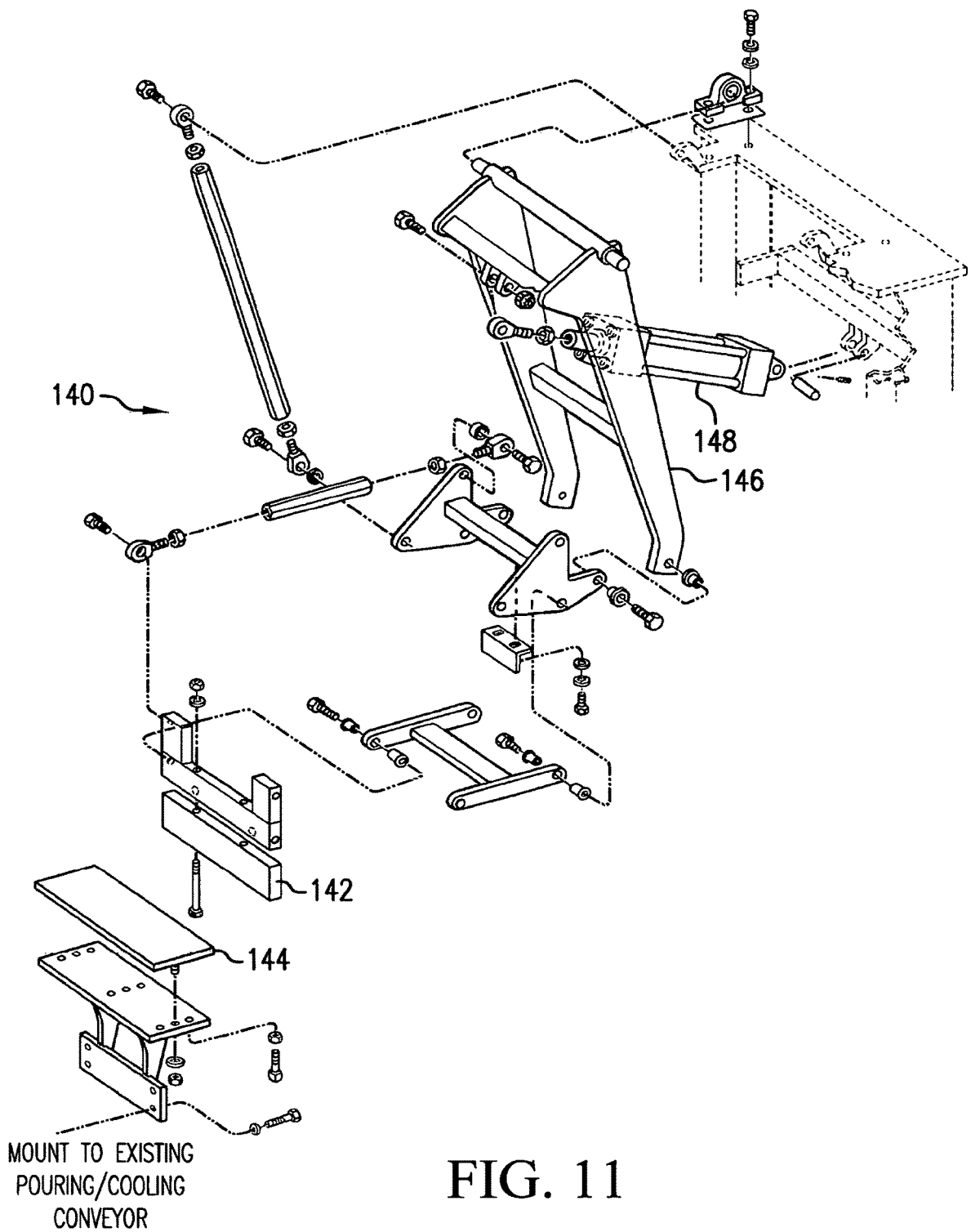

Accumulating mold conveyor 20 includes second junction resting station 90 disposed at the downstream end 36 of second transfer conveyor 24 and within the lifting and transfer station 55. Second junction resting station 90 is similar in configuration and function to first junction resting station 86. Second junction resting station 90 includes four spaced apart resting pads 92 for holding sand molds 25. The lift platform 45 includes an X- or cross-shaped configuration with extensions that fit and lift between pairs of the four pads 92 to lift the mold vertically (perpendicular to the conveying direction) to the pusher 40. Pusher 40, which can include a hydraulically activated pusher arm, pushes sand molds 25 off the second junction resting station 90 and onto a receiving surface/platform (e.g., add-on platform 144 of FIG. 11) of the associated station 18.

This invention further includes a method for conveying a sand mold. The method of this invention uses an accumulating conveyor, such as described above, including a first transfer conveyor in conveying combination with a second transfer conveyor, each of the first and second transfer conveyors comprising two outboard rails and a central transfer rail movable between the two outboard rails.

In one embodiment of this invention, referring to FIG. 1, a first sand mold forming machine deposits first sand mold 25 on first transfer conveyor 22. In one embodiment of this invention, sand mold 25 is placed directly onto first transfer conveyor 22, without an optional bottom board, such as are known to those skilled in the art. Sand mold 25 moves along first transfer conveyor 22 in a first downstream direction. First transfer conveyor 22 moves sand mold 25 by lifting the sand, mold off outboard rails 46 and 48 with central transfer rail 52, moving central transfer rail 52 and the lifted sand mold 25 in the first downstream direction, and lowering the lifted sand mold 25 onto outboard rails 46 and 48. The steps for moving first sand mold 25 are repeated until first sand mold 25 is placed by central transfer rail 52 onto first junction resting station 86. Upon placing first sand mold 25 onto first junction resting station 86, central transfer rail 52 moves back upstream and out from under sand mold 25.

Central transfer rail 52' of second transfer conveyor 24 then moves under first sand mold 25 to transfer first sand mold 25 to second transfer conveyor 24. Central transfer rail 52' lifts first sand mold 25 off first junction resting station 86 and moves first sand mold 25 along second transfer conveyor 24 in the manner discussed above for first transfer conveyor 22, but in a second downstream direction, that is perpendicular to the downstream direction of first transfer conveyor 22. The steps for moving first sand mold 25 along second transfer conveyor 24 are incrementally repeated until first sand mold 25 is placed by central transfer rail 52 onto second junction resting station 90. Upon placing first sand mold 25 onto second junction resting station 90, central transfer rail 52 moves back upstream and out from under first sand mold 25.

FIGS. 6-11 illustrate a lift and transfer station 120, such as for the end of the conveyor 20 of FIG. 1 or 2. As discussed above, the lift and transfer station 120 is useful for moving molds to a destination station 18 having a different height from the origination station 16. The station 120 includes a station frame 122 extending above the conveyor 20, such as positioned at or around the last shuttle position at the end 36 of the conveyor 20.

Figure 9:
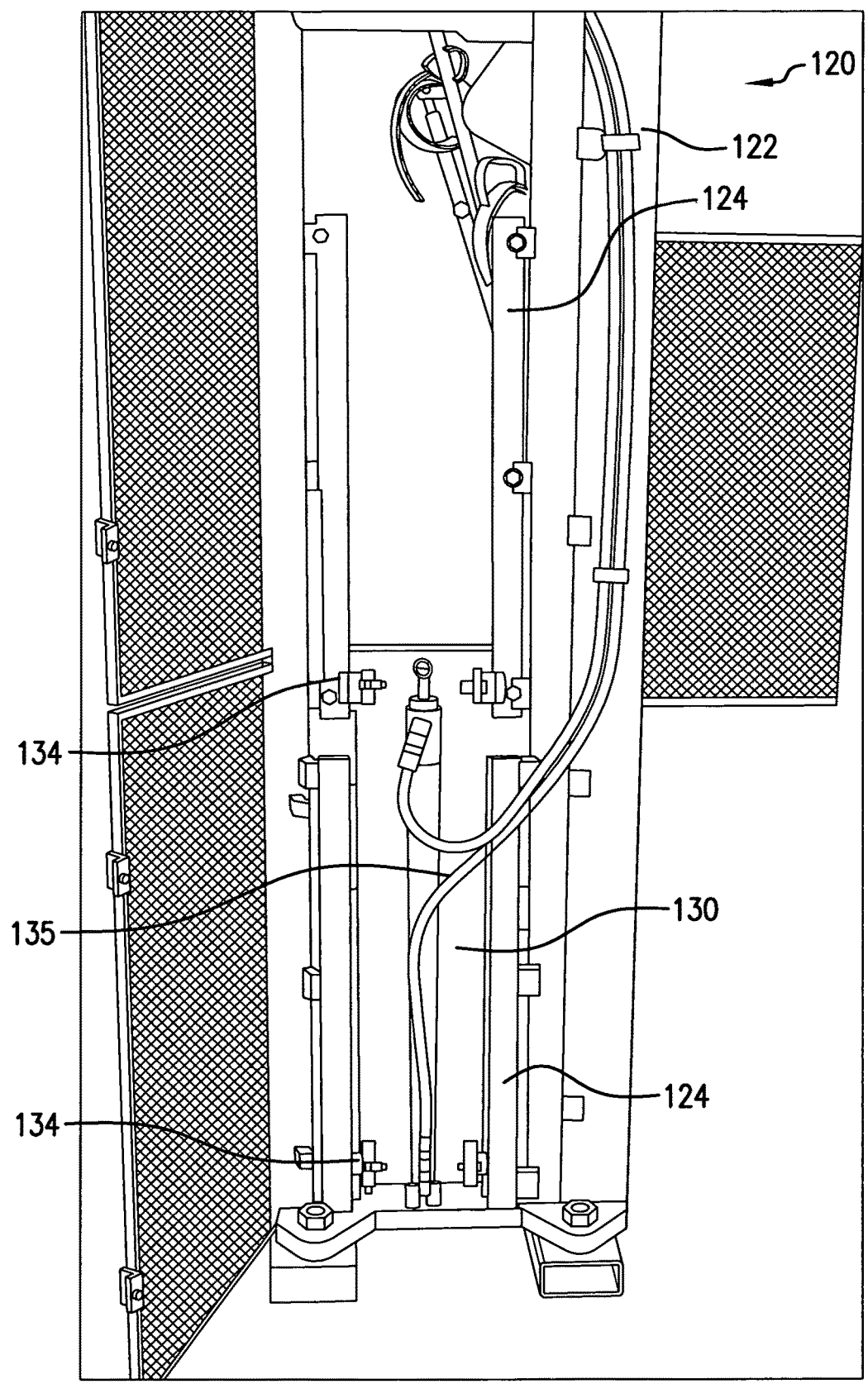
Figure 10:
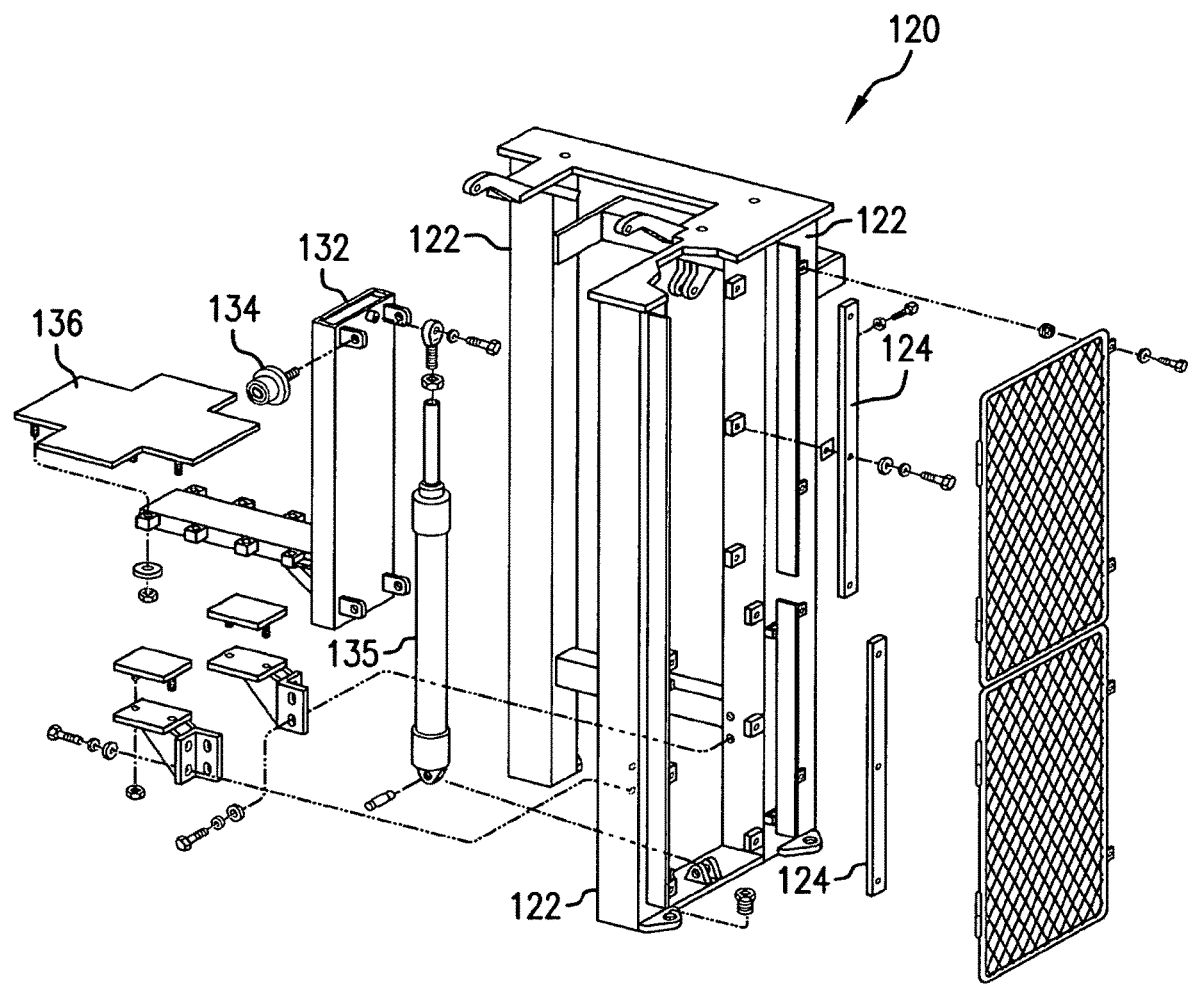

The station 120 includes a mold lift mechanism 130 attached to the frame 120. The mold lift mechanism 130 includes a lift frame 132 attached by pressurized fluid lift cylinder 135 to the station frame 122. As shown in FIGS. 9 and 10, the lift frame 132 includes rollers 134 that ride on lift rails 124 attached to the station frame 122. In the illustrated embodiment, pairs of lift rails are offset from each other, with one, lower pair of rollers disposed on an inner side of a first pair of lift rails 124, and a second, upper pair of rollers disposed on an outer side of a second pair of lift rails 124.

Figure 7:
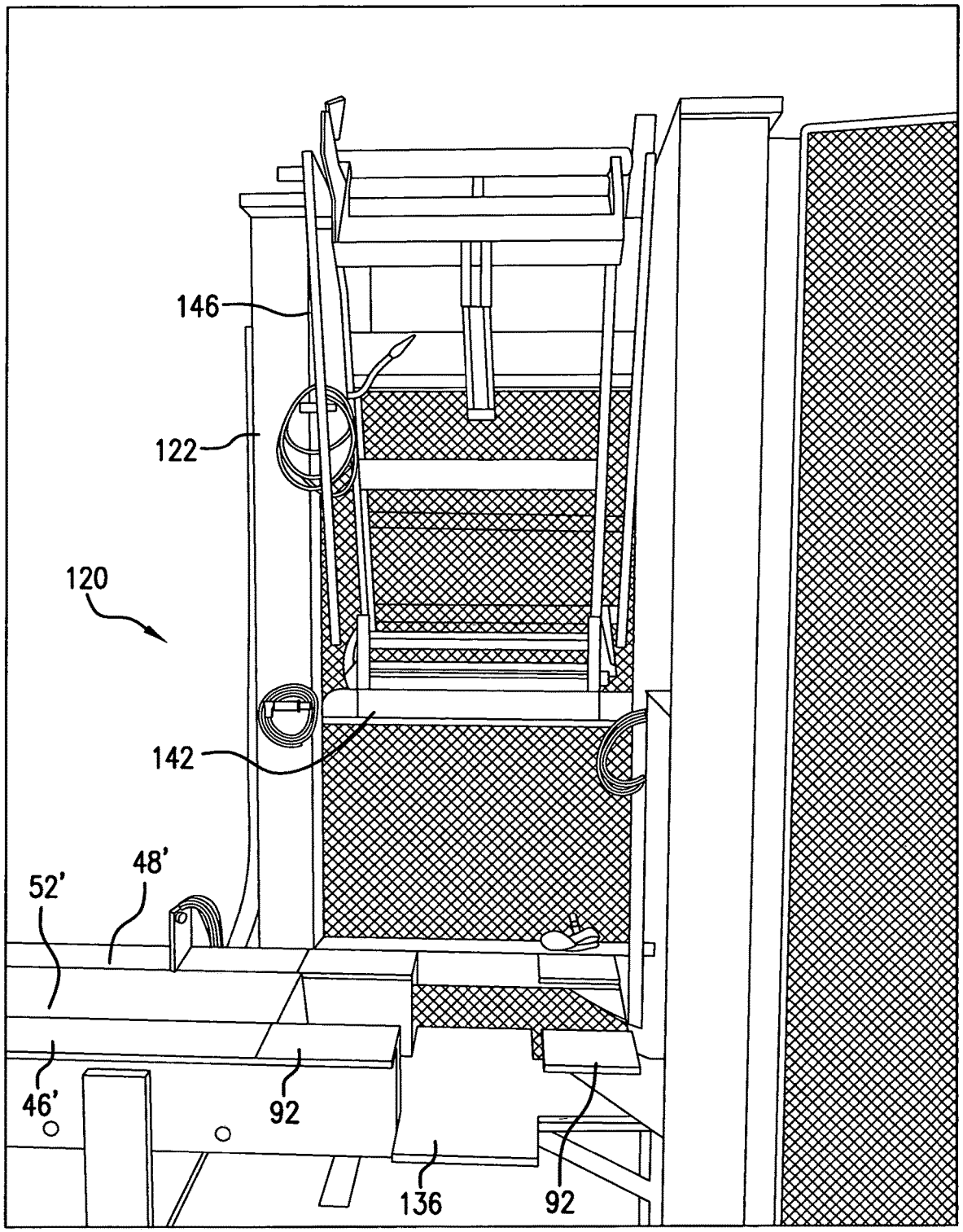
Figure 8:
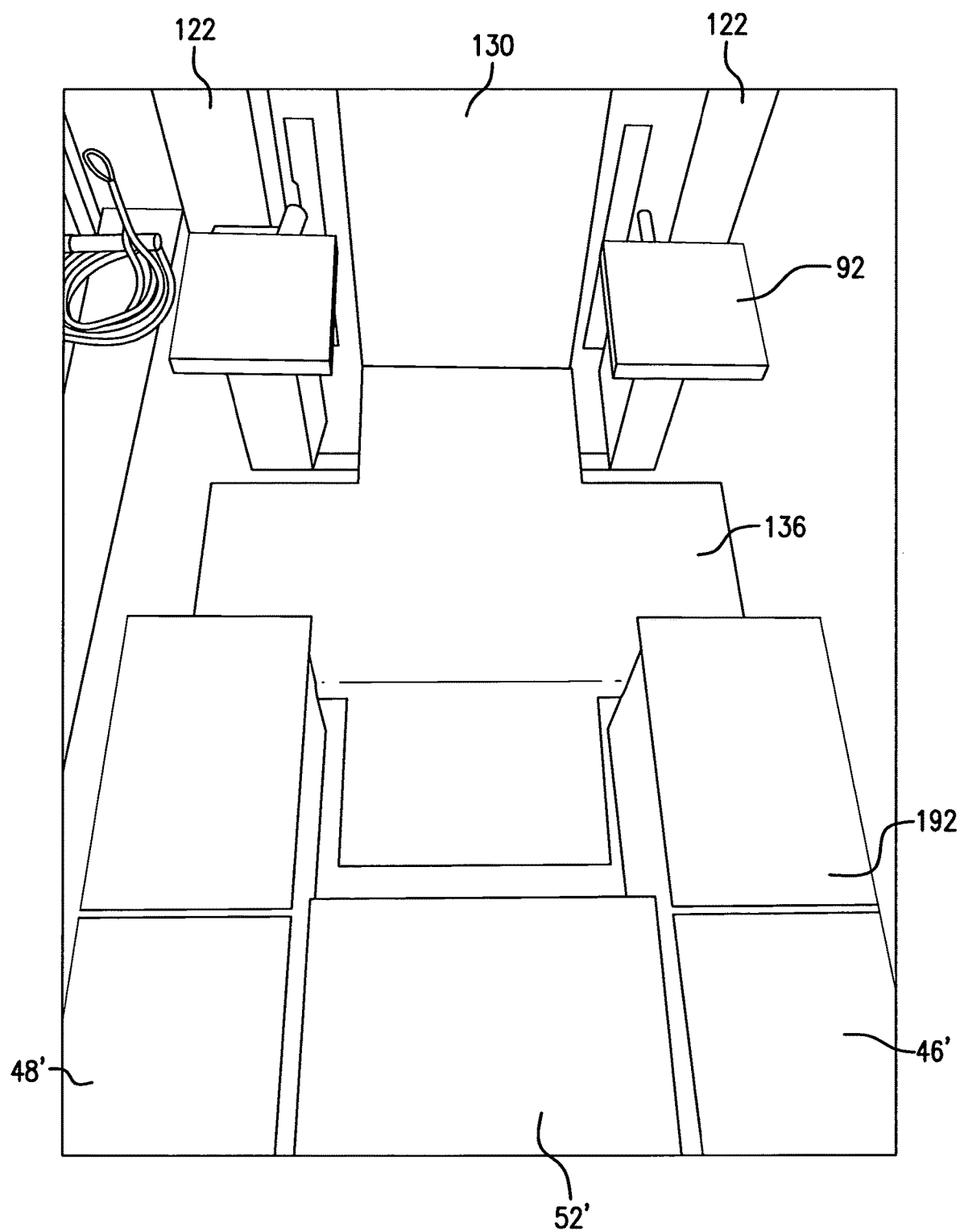

The mold lift mechanism 130 includes a lift platform 136 that contacts the mold 25 from below and lifts the mold to the desired transfer height above the conveyor 20. As discussed above, the lift platform 136 includes a cross- or X-shape that fits between the four corner pads 92 of the conveyor end 36. As shown in FIG. 7, the lift platform 136 is lowerable to a position that allows the transfer rail 52' to roll above the platform 136 to place the mold on the pads 92 for lifting.

The station 120 further includes a pusher mechanism 140. The pusher mechanism 140 includes a transfer pusher or blade 142 positioned at a transfer height of the lift mechanism 130. The transfer pusher 142 is parallel to the transfer rail 52' and 'pushes' in a direction perpendicular to the conveying path of transfer rail 52'. Upon the lift platform 136 raising into the necessary vertical position, the pusher 142 pushes the mold laterally to the station 18. In embodiments of this invention, the pusher 142 pivots about a pusher frame attachment 146 to the station frame 122, such as powered via a pressurized fluid cylinder 148.

As will be appreciated by those skilled in the art following the teachings herein provided, various and alternative sizes, shapes, and configurations are available for the mold accumulating conveyor, transfer conveyors, junction resting stations, leveling mechanisms, lift mechanisms, and pusher mechanisms, of this invention.

Thus, the invention provides a mold accumulating conveyor that feeds sand molds from multiple sand mold forming machines to a single metal pouring station. The accumulating mold conveyor of this invention improves efficiency of casting by, for example, allowing for a sand mold casting apparatus to continually run, even while one associated sand mold forming machine is offline. The invention further provides a more flexible accumulating mold conveyor installation, such as between machine stations or two different manufacturers. The apparatus and method allows for moving the sand mold onto and/or off of the accumulating conveyor in a direction lateral to a conveying direction of the accumulating conveyor and/or at a vertical height different from an entry height.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. An apparatus for conveying a sand mold, the apparatus comprising:
    an accumulating conveyor including a transfer rail movable with respect to at least one fixed rail, wherein the accumulating conveyor comprises an adjustment mechanism in combination with the transfer rail, the adjustment mechanism configured to adjust a horizontal alignment of the transfer rail with respect to the at least one fixed rail; and
    a device for moving the sand mold onto and/or off of the accumulating conveyor in a direction lateral to a conveying direction of the accumulating conveyor and/or at different vertical heights.

2. The apparatus of claim 1, wherein the device comprises a pusher that travels in the direction lateral to the conveying direction.

3. The apparatus of claim 1, wherein the adjustment mechanism comprises a leveling cylinder that moves vertically in a direction perpendicular to the conveying direction.

4. The apparatus of claim 3, wherein the leveling cylinder of the adjustment mechanism is connected on a conveyor frame and under a rail frame of the transfer rail.

5. The apparatus of claim 1, further comprising a transfer station at an end of the accumulating conveyor, and including the device for moving the sand mold.

6. The apparatus of claim 5, wherein the transfer station comprises a mold lift that moves vertically in a direction perpendicular to the conveying direction, wherein the mold lift raises the sand mold to a pusher of the device for the moving the sand mold.

7. The apparatus of claim 6, wherein the mold lift comprises a cross-shape or X-shape lift platform with two extensions that extend between pairs of four corner pads of an accumulating conveyor end.

8. The apparatus of claim 6, wherein the mold lift comprises a lift platform adapted to lower below the at least one fixed rail to allow the transfer rail to move the sand mold into position over the lift platform.

9. An apparatus for conveying a sand mold, the apparatus comprising:
an accumulating conveyor including a transfer rail movable with respect to at least one fixed rail; and
a transfer station at a downstream end of the accumulating conveyor, the transfer station including a mold lift platform and a pusher, wherein the mold lift platform is configured to raise the sand mold off the at least one fixed rail into a position adjacent the pusher.

10. The apparatus of claim 9, wherein the mold lift platform is adapted to lower below the at least one fixed rail to allow the transfer rail to move the sand mold into position over the mold lift platform.

11. The apparatus of claim 9, wherein the transfer station comprises a frame extending above the accumulating conveyor, the mold lift platform moves vertically along the frame, and the pusher is pivotably connected to an upper section of the frame.

12. The apparatus of claim 9, wherein the accumulating conveyor comprises an adjustment mechanism in combination with the transfer rail, the adjustment mechanism configured to adjust a horizontal alignment of the transfer rail with respect to at least one fixed rail.

13. The apparatus of claim 12, wherein:
the transfer rail comprises a rail frame and a plurality of sand mold carrier plates each connected to the rail frame by a corresponding pressurized fluid lift mechanism; and
the adjustment mechanism comprises a leveling cylinder on a conveyor frame and under the rail frame of the transfer rail, and the leveling cylinder is configured to lift the rail frame relative to the conveyor frame.

14. A method for conveying a sand mold with the apparatus according to claim 9, the method comprising:
moving the sand mold with the accumulating conveyor via the transfer rail reciprocating with respect to the at least one fixed rail; and
moving the sand mold onto and/or off of the accumulating conveyor in a direction lateral to a conveying direction of the accumulating conveyor and/or at the different vertical heights.

15. The method of claim 14, further comprising pushing the sand mold with the pusher, wherein the pusher travels in the direction lateral to the conveying direction.

16. The method of claim 14, further comprising adjusting a horizontal alignment of the transfer rail with respect to the at least one fixed rail, wherein the adjusting comprises moving a leveling cylinder under the transfer rail vertically in a direction perpendicular to the conveying direction.

17. The method of claim 14, further comprising:
moving the sand mold to the transfer station at the downstream end of the accumulating conveyor; and
lifting the sand mold to the pusher.

18. The method of claim 17, wherein the mold lift platform comprises a cross-shape or X-shape lift platform with two extensions that extend between pairs of four corner pads of the downstream end of the accumulating conveyor.

19. The method of claim 17, further comprising:
lowering the mold lift platform below the at least one fixed rail; and
moving the transfer rail with the sand mold into position over the mold lift platform.

20. The apparatus of claim 9, wherein the mold lift platform comprises a cross-shape or X-shape lift platform with two extensions that extend between pairs of four corner pads of an accumulating conveyor end.

\* \* \* \* \*